(12) United States Patent
Fujisawa et al.

(10) Patent No.: US 7,683,206 B2
(45) Date of Patent: Mar. 23, 2010

(54) SILICONE COMPOUND AND PROCESS FOR PRODUCING THE SAME

(75) Inventors: Kazuhiko Fujisawa, Shiga (JP); Tsutomu Goshima, Shiga (JP); Mitsuru Yokota, Shiga (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 10/590,850

(22) PCT Filed: Feb. 25, 2005

(86) PCT No.: PCT/JP2005/003101

§ 371 (c)(1),
(2), (4) Date: Aug. 25, 2006

(87) PCT Pub. No.: WO2005/090364

PCT Pub. Date: Sep. 29, 2005

(65) Prior Publication Data

US 2007/0191621 A1    Aug. 16, 2007

(30) Foreign Application Priority Data

Feb. 27, 2004 (JP) ............................. 2004-053435

(51) Int. Cl.
C07F 7/08 (2006.01)
C07C 30/08 (2006.01)
C08G 77/38 (2006.01)

(52) U.S. Cl. .................................................... 560/205

(58) Field of Classification Search .................. None
See application file for complete search history.

(56) References Cited

U.S. PATENT DOCUMENTS 5,891,356 A * 4/1999 Inoue et al. ................... 252/73
2004/0198916 A1 * 10/2004 Nakamura et al. ....... 525/329.4

FOREIGN PATENT DOCUMENTS

JP      56022325       *    3/1981
JP    2002080538       *    3/2002

OTHER PUBLICATIONS

Sigma-Aldrich Specification Sheet for Potassium Hydroxide ACS reagent.*

* cited by examiner

Primary Examiner—Paul A Zucker
Assistant Examiner—Yevegeny Valenrod
(74) Attorney, Agent, or Firm—Pillsbury Winthrop Shaw Pittman LLP

(57) ABSTRACT

This invention provides a process for producing of a silicone compound which includes a synthesis reaction of a silicone compound represented by the following formulas (a) and/or (a'),

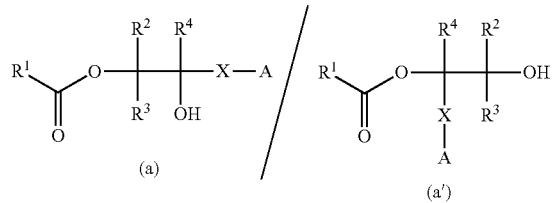

by reacting a carboxylic acid represented by the following formula (a2)

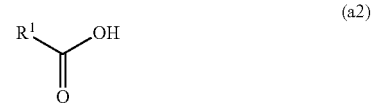

to an epoxy silane represented by the following formula (a1)

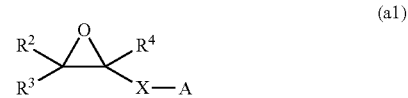

in presence of a metal salt of the carboxylic acid represented by the general formula (a2), characterized in that the reaction is carried out in presence of 0.05 wt % or more water in said reaction system. Here, A denotes siloxanyl group. $R^1$ denotes a substitutent with 1 to 20 carbons having a polymerizable group. $R^2$ to $R^4$ respectively and independently denote hydrogen, a substituted or unsubstituted substitutent with 1 to 20 carbons, or —X-A. X denotes a substituted or unsubstituted divalent substitutent with 1 to 20 carbons.

6 Claims, No Drawings

SILICONE COMPOUND AND PROCESS FOR PRODUCING THE SAME

REFERENCE TO RELATED APPLICATION

This application is a U.S. National Stage Application of International Application No. PCT/JP05/003101 which was filed Feb. 25, 2005, and which claims the benefit of priority to Japanese Application No. 2004-053435, filed Feb. 27, 2004.

TECHNICAL FIELD

This invention relates to a silicone compound which provides a polymer preferably used for ophthalmic lens applications such as a contact lens, an intraocular lens and an artificial cornea, and a production method thereof.

BACKGROUND ART

Conventionally, as monomers which provide polymers used for ophthalmic lenses, compounds having a silicon group have been known.

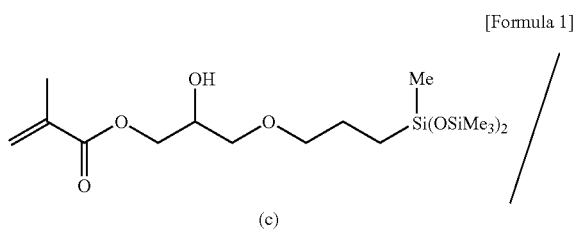

[Formula 1]

(c)

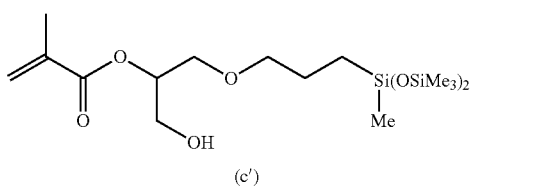

(c')

As one of such compounds, those shown in the above-mentioned formula (c) or (c') are known (for example, patent reference 1). This compound has a feature to be easily compatible with a hydrophilic monomer since it has a hydroxyl group in its molecule, and there is a well-known synthetic method thereof (patent reference 1). However, by the method described in the patent reference 1, even if various reaction conditions are tested, purity can be increased to only from 85% to about 89%, but a higher purity has been desired.

Patent reference 1: JP-A-S56-22325, Example 4

DISCLOSURE OF THE INVENTION

Problem(s) to be Solved by the Invention

Under such circumstances, we, inventors, intensively investigated and found, as a reason for that the low purity couldn't be improved, compounds represented by the following formula (x) or (x') are contained most as byproducts.

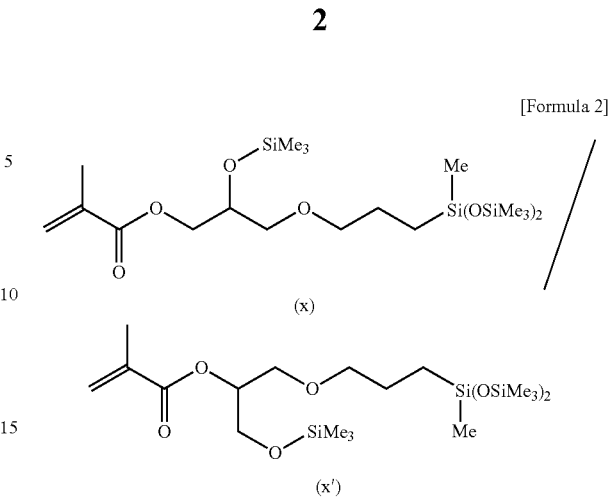

[Formula 2]

(x)

(x')

Since these byproducts have polarities or boiling points close to those of the compound to be produced, it was difficult to remove by any of column purification and by distillation purification, and caused a difficulty of improving the purity.

Moreover, in the field of ophthalmic lenses, such as a contact lens, it is needless to say that impurities are preferably as few as possible, but even if impurities are few, it is necessary that the impurities are not problematic to users. For that reason, if there is an impurity, it is necessary to know properties of the impurity, but if, as a method for improving purity, a method is applied in which the impurity is converted to the compound to be produced, another new impurity may be produced.

This invention aims to provide a method for producing the silicone compound represented by the general formula (a) or (a') which can be obtained in a high purity and is useful as a raw material for ophthalmic lenses such as contact lens.

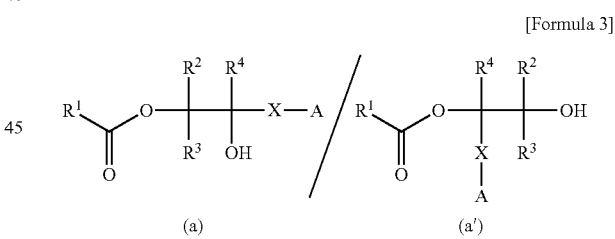

[Formula 3]

(a)      (a')

(Here, A denotes a siloxanyl group. $R^1$ denotes a substitutent with 1 to 20 carbon atoms having a polymerizable group. $R^2$ to $R^4$ respectively and independently denote hydrogen, a substituted or unsubstituted divalent substitutent with 1 to 20 carbons or —X-A. X denotes a substituted or unsubstituted substitutent.)

Means for Solving the Problem

In order to solve the above-mentioned problem, this invention has the following constitution. That is, the present invention is;

(1) A production method of a silicone compound which includes a synthesis reaction of a silicone compound represented by the following general formulas (a) and/or (a'),

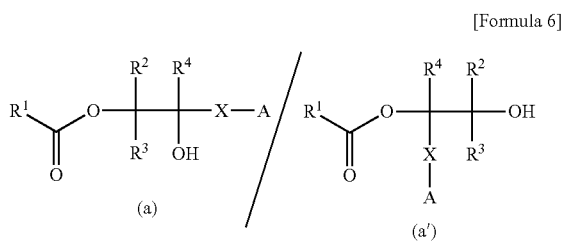

by reacting a carboxylic acid represented by the following general formula (a2)

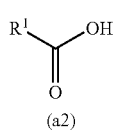

to an epoxy silane represented by the following general formula (a1)

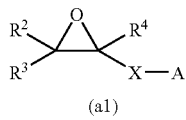

in presence of a metal salt of a carboxylic acid represented by the general formula (a2), characterized in that the reaction is carried out in presence of 0.05 wt % or more water in said reaction system.

(Here, A denotes a siloxanyl group. $R^1$ denotes a substitutent with 1 to 20 carbons having a polymerizable group. $R^2$ to $R^4$ respectively and independently denotes hydrogen, a substituted or unsubstituted substitutent with 1 to 20 carbons, or —X-A. X denotes a substituted or unsubstituted divalent substitutent with 1 to 20 carbons.)

(2) A production method of a silicone compound characterized in that the silicone compound obtained by the method described in the above item (1) is purified by a silica gel column or an alumina column.

(3) A silicone compound obtained by the production method described in the above item (1) or (2), wherein the siloxanyl group A is an atomic group represented by the following formula (b).

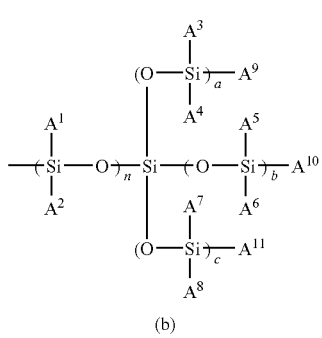

[In the formula (b), $A^1$ to $A^{11}$ respectively and independently denote any one of hydrogen, a substituted or unsubstituted alkyl group with 1 to 20 carbon atoms and a substituted or unsubstituted aryl group with 6 to 20 carbons. n denotes an integer of 0 to 200, a, b and c denote respectively and independently an integer of 0 to 20. However, the case of n=a=b=c=0 not included.]

(4) A silicone compound described in the above item (3), wherein the siloxanyl group A is selected from the group consisting of tris(trimethylsiloxy)silyl group, bis (trimethylsiloxy)methylsilyl group and trimethylsiloxydimethylsilyl group.

(5) A silicone compound in which a content of the compound represented by the following general formula (y) is 0.4% or more and 3% or less,

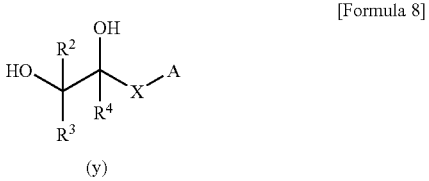

and the purity of the silicone compound represented by the following general formulas (a) and/or (a') is 87% or more.

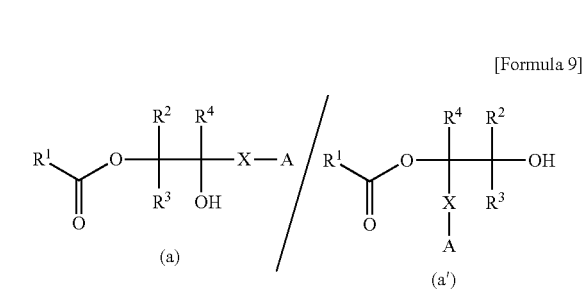

(Here, A denotes a siloxanyl group. $R^1$ denotes a substitutent with 1 to 20 carbons having a polymerizable group. $R^2$ to $R^4$ respectively and independently denotes hydrogen, a substituted or unsubstituted substitutent with 1 to 20 carbons, or —X-A. X denotes a substituted or unsubstituted divalent substitutent with 1 to 20 carbons.)

Effect of the Invention

According to the present invention, it is possible to obtain the silicone compound represented by the general formula (a) and/or (a') in high purity, and the obtained compound can be preferably used as a monomer to provide a preferable polymer for ophthalmic lenses such as a contact lens.

BEST EMBODIMENT FOR CARRYING OUT THE INVENTION

In the present invention, the compounds represented by the general formulas (a) and/or (a') are obtained from the compound represented by the general formula (a1) and the compound represented by the general formula (a2) as raw materials.

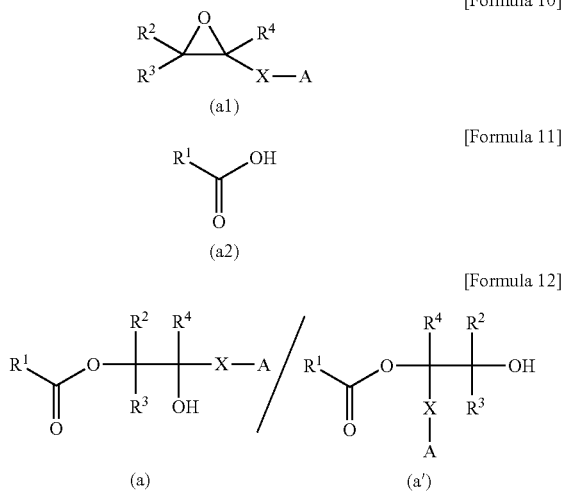

In the compounds represented by the general formula (a) and/or (a'), $R^1$ denotes a substitutent with 1 to 20 carbons having a polymerizable group. This is originated from the compound represented by the general formula (a2).

The polymerizable group means carbon-carbon double bond capable of radical polymerization. As examples of the compound represented by the general formula (a2) which gives $R^1$, vinyloxy acetic acid, allyloxy acetic acid, (meth) acrylic acid, crotonic acid, 2-(meth)acryloyl propanoic acid, 3-(meth)acryloyl butanoic acid, 4-vinyl benzoic acid, etc. can be mentioned. Among them, since it is easy to obtain corresponding carboxylic acid salts which function also as catalysts at synthesizing the silicone monomers (a) and/or (a'), acrylic acid and methacrylic acid can most preferably be used. It is preferable that the compound represented by the general formula (a2) is used in the range of 1 to 50 equivalents per epoxy silane (compound represented by the general formula (a1)), and in order not to leave epoxy silane, 1.5 to 40 equivalents are more preferable, and in consideration of cost, it is most preferable to add 2 to 30 equivalents.

$R^2$ to $R^4$ denotes respectively and independently hydrogen, a substituted or unsubstituted substitutent with 1 to 20 carbons or —X-A. X denotes a substituted or unsubstituted aliphatic or aromatic divalent substitutent with 1 to 20 carbons. A denotes a siloxanyl group. The siloxanyl group in this specification means a group having at least one Si—O—Si bond. As the siloxanyl group, the substitutent represented by the following formula (b) is preferably used because of availability of its raw material or easiness of synthesis.

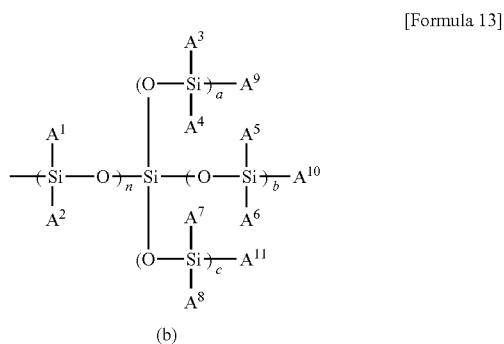

[In the formula (b), $A^1$ to $A^{11}$ respectively and independently denote any one of hydrogen, a substituted or unsubstituted alkyl group with 1 to 20 carbon atoms and a substituted or unsubstituted aryl group with 6 to 20 carbons. n denotes an integer of 0 to 200, and a, b and c denote respectively and independently an integer of 0 to 20. However, the case of n=a=b=c=0 is not included.]

In the formula (b), as $A^1$ to $A^{11}$, respectively and independently hydrogen, alkyl groups such as methyl group, ethyl group, propyl group, isopropyl group, butyl group, isobutyl group, sec-butyl group, tert-butyl group, hexyl group, cyclohexyl group, 2-ethylhexyl group and octyl group, aryl groups such as phenyl group and naphthyl group, can be mentioned. Among these, methyl group is most preferable.

In the formula (b), n is an integer of 0 to 200, but preferably 0 to 50, more preferably 0 to 10. a, b and c are respectively and independently, an integer of 0 to 20, but preferably respectively and independently an integer of 0 to 5. In case of n=0, preferable combination of a, b and c is a=b=c=1, or a=b=1 and c=0.

Among the substitutents represented by the formula (b), because compounds having such substitutents are industrially available with ease, tris(trimethylsiloxy)silyl group, bis(trimethylsiloxy)methylsilyl group, trimethylsiloxydimethylsilyl group, polydimethylsiloxane group, polymethylsiloxane group, poly-co-methylsiloxane-dimethylsiloxane group, etc., are especially preferable.

In the production method of the silicone compound of the present invention, metal salt of the carboxylic acid represented by the above-mentioned formula (a2), preferably, metal salt of acrylic acid or methacrylic acid, preferably alkali metal salt is used as a catalyst. An amount to be added of the catalyst is preferably 0.001 to 5 equivalents per epoxy silane as raw material (compound represented by the above-mentioned general formula (a1)), more preferably 0.005 to 3 equivalents, and most preferably 0.01 to 1 equivalent.

In the present invention, it is characterized in that, in the reaction system to obtain the compound represented by the general formulas (a) and/or (a') from the compounds represented by the above-mentioned general formula (a1) and represented by the general formula (a2), the reaction is carried out in presence of 0.05 wt % or more water in the reaction system, namely, as the ratio occupied in total component of the reaction systems. If the reaction is carried out in the presence of no water, or less than 0.05 wt % water, a byproduct, compound represented by the general formulas (z) and/or (z') generates, and since this byproduct is difficult to dissociate, as a result, it is impossible to achieve a high purity production.

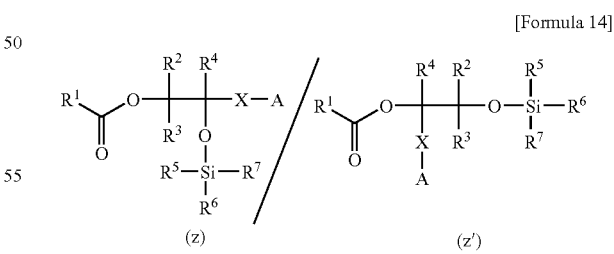

On the other hand, according to the present invention, even if the compound represented by the general formulas (z) and/or (z') generates, since a hydrolysis reaction by the water present in the system takes place in parallel to the synthesis reaction, it is possible to reduce the production amount of the byproduct to thereby improve the purity of the silicone compound. Here, the components used for the production method of the present invention such as the metal salt of carboxylic acid represented by the above-mentioned general formula (a2) may have absorbed moisture. The water content defined in the present invention is the content including water content carried in by such a moisture absorbed component. The water content contained in the moisture absorbed component can be determined by difference with the dry weight, for example, by drying by a method such as vacuum drying at 40° C. for 14 hours.

Here, as for the compound represented by the above-mentioned general formula (z) and/or (z'), when desilylation is carried out by ordinary desilylation condition after termination of the synthesis reaction, for example, by adding carboxylic acid-methanol, it is possible to improve purity of the above-mentioned general formula (a) and/or (a') by decomposing the compound represented by the general formula (z) and/or (z'), but in this case, other than that it is economically disadvantageous due to increase of the desilylation step, there is a problem that it generates other impurity because siloxanyl group portion also decompose in parallel to the desilylation reaction.

In particular, for polymers used for an ophthalmic lens such as contact lens which is a medical device, even a little amount of an impurity is present, verification of safety of the impurity is required, accordingly, it is best that the amount of such an impurity is as little as possible.

According to the production method of the present invention, perhaps because of simultaneous advance, with the reaction, of the decomposition of the compound represented by the above-mentioned general formulas (z) and/or (z'), said compound, as an impurity, is reduced significantly, and a possibility of producing a new impurity is also low, to thereby make it possible to improve the purity.

If the amount of water to be present in the reaction system is too small, the compound represented by the above-mentioned general formula (z) and/or (z') will remain and a sufficient effect of improving purity cannot be obtained, on the contrary, if it is too much, not only a further improvement of purity is not expected since the compound represented by the general formula (z) and/or (z') is completely consumed, but also the compound represented by the following general formula (y) is produced by the reaction of the raw material, the compound represented by the general formula (a1), and water,

[Formula 15]

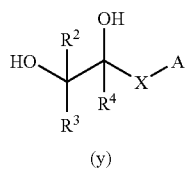

(y)

to result in a fall of purity. Accordingly, it is preferable to be 0.05 to 5 wt %, more preferable to be 0.1 to 3 wt %, most preferable to be 0.3 to 2 wt %. That is, it is preferable that the upper limit is 5 wt % or less, more preferably 3 wt % or less, still more preferably 2 wt % or less, and it is preferable that the lower limit is 0.05 wt % or more, more preferably 0.3 wt % or more.

In the production method of the silicone compound of the present invention, in order to prevent polymerization of the silicone compound during the synthesis reaction, the synthesis reaction may be carried out under presence of a polymerization inhibitor. As examples of the polymerization inhibitor, hydroquinone, hydroquinone monomethyl ether, 2,6-di-t-butyl-4-methyl phenol, and N-nitrosophenyl hydroxylamine aluminum, etc., can be mentioned. And, the amount of the polymerization inhibitor when it is used, 0.0005 to 5 wt % based on the amount of the carboxylic acid represented by the above-mentioned general formula (a2), for example, based on the amount of (meth)acrylic acid, is preferable, 0.001 to 3 wt % is more preferable, and 0.005 to 1 wt % is most preferable.

If the reaction temperature in the production method of the silicone compound of present invention is too low, the reaction time becomes too long, and if it is too high, there is a danger that the silicone compound would polymerize during the synthesis reaction. Accordingly, 50 to 180° C. is preferable, 60 to 170° C. is more preferable and 70 to 160° C. is most preferable.

The purity of the silicone compound obtained by the production method of the silicone compound of the present invention (defined as the areal % determined by gas chromatographic measurement mentioned later) is preferably 89% or more, and more preferably 90% or more. The upper limit is not especially limited, but in consideration of productivity due to complexity and many steps of the purification process, and a sufficient purity for use of an ophthalmic lens, 99% or less, if allowed, about 97% or less is a goal for the moment.

Since the silicone compound obtained by the production method of the present invention is synthesized in the presence of water in the reaction mixture, an amount of the compound represented by the above mentioned general formula (y) may increase by the reaction between the raw material represented by the above-mentioned general formula (a1) and water. Since the compound represented by the general formula (y) has no polymerizable group in its molecule, it may be contained as it is in the polymer obtained by polymerizing the silicone compound of the present invention, but as for removal of such a compound, by silica gel column, alumina column, etc., the compound represented by the above-mentioned general formula (y) can be removed. By subjecting to such treatments, it is possible to reduce the amount of impurity such as the compound represented by the general formula (y), and can be obtained as a silicone compound capable of providing a preferable polymer for use as an ophthalmic lens such as a contact lens in which impurity is few and purity is high.

In the present invention, the amount of the compound represented by the above-mentioned general formula (y) is, as the areal % determined by gas chromatographic measurement mentioned later, 0.4% or more, and 3% or less. If the production amount of the compound represented by the general formula (y) is large, because it can reduce the production amount of the compound represented by the above-mentioned general formulas (z), (z') of which production amount is basically large, it is possible to improve the purity. That is, by making the amount represented by the general formula (y) 0.4% or more, it is possible to easily improve the purity to 87% or more.

It is preferable that the amount of the compound represented by the above-mentioned general formula (y) after purified by the silica gel column or alumina column is 0.7 wt % or less, and in order to use the polymer obtained by polymerizing said silicone compound for an ophthalmic lens, 0.6 wt % or less is preferable, and in order to use said polymer for a soft contact lens, 0.5 wt % or less is preferable. Here, the amount of the compound represented by the general formula (y) can be determined by a calibration curve method in which a standard substance is used in gas chromatographic measurement mentioned later.

When the monomer of the present invention is polymerized, the silicone compound of the present invention may be polymerized alone, or copolymerized with other component. In addition, publicly known polymerization methods can be applied, for example, the polymerization can be done by addition of a heat-polymerization initiator such as represented by peroxide and azo compound or photo-polymerization initiator. And, if necessary, it is possible to use a solvent. As molding method for molding ophthalmic lenses such as a contact lens, an intraocular lens and an artificial cornea, publicly known methods can also be applied. For example, a method of polymerizing in a shape of rod or plate at first and then processing into a desired form by cutting, etc., a mold polymerization method in which molding and polymerization is done simultaneously in a mold made of materials such as plastic, metal and quartz, etc., are mentioned.

The polymer obtained by polymerizing the silicone compound produced by the production method of the present invention is especially preferable as ophthalmic lenses such as a contact lens, an intraocular lens and an artificial cornea.

EXAMPLE

Hereafter, the present invention is explained concretely with reference to examples, but the present invention is not limited thereby.

Measuring Method

Gas Chromatographic Measurement (Hereafter, May be Abbreviated as GC)

For GC measurement, GC-18A (FID detector) produced by Shimazu Corp. as main body, DB-5 (0.25 mm×30 m×1 μm) produced by J&W Scientific Inc. as capillary column, were used. The measurement was carried out with helium as carrier gas (138 kPa), inlet temperature of 280° C., detector temperature of 280° C. and a temperature elevation program of 60° C. (5 min.) –>10° C./min. –>325° C. (19 min.). The sample was prepared by dissolving 100 μl of a material to be measured in isopropyl alcohol 1 ml, and 1 μl thereof was injected.

Example 1

The epoxy silane represented by the following formula (c1) 100 g (0.3 mol),

[Formula 16]

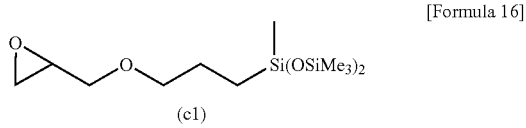

(c1)

methacrylic acid 103.4 g (1.2 mol), sodium methacrylate 9.6 g (0.09 mol), p-methoxyphenol 5.5 g (0.04 mol) and water 3.6 g were put into a 300 ml eggplant type flask, heated to 100° C. and stirred in air atmosphere. After confirming by GC that the areal % of epoxy silane becomes 0.1% or less, the reaction mixture was cooled to room temperature. Hexane 150 ml was added to the reaction mixture, the hexane solution was washed three times with 250 ml of 0.1N aqueous solution of sodium hydroxide and three times with 175 ml of 2.6% aqueous solution of table salt, dried by addition of sodium sulfate to the organic layer, filtered and removed the solvent by an evaporator to obtain a liquid of 126 g. GC of the obtained liquid was measured and the results shown in Table 1 were obtained. The obtained liquid was purified in a column with silica gel 190 g and hexane/ethyl acetate=4/1, distilled off the solvent and the obtained liquid was subjected to GC measurement to obtain the results shown in Table 1.

As a result of reducing the amount of the compound represented by the general formula (z) and/or (z'), a high purity was attained, and even though the component (y) increased, since it is a component removable by column purification, purity improvement effect of 1% or more was attained.

Example 2

An experiment was carried out in the same way as Example 1, except changing the epoxy silane to the compound represented by the following formula (d1)

[Formula 17]

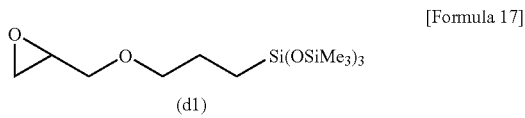

(d1)

and the amount of water to be added to the amounts shown in Table 1. By GC measurement, the results shown in Table 1 were obtained.

Example 3

An experiment was carried out in the same way as Example 1, except changing the amount of water to be added to the amount shown in Table 1. By GC measurement, the results shown in Table 1 were obtained.

Example 4

An experiment was carried out in the same way as Example 1, except changing the amount of water to be added to the amount shown in Table 1. By GC measurement, the results shown in Table 1 were obtained.

Comparative Example 1

An experiment was carried out in the same way as Example 1, except adding no water. By GC measurement, the results shown in Table 1 were obtained. The amount of the compound represented by the general formulas (z) and/or (z') was very large compared to the cases in which water was added, and the purity was low.

Comparative Example 2

An experiment was carried out in the same way as Example 1, except adding no water, and to the obtained liquid of silicone compound, three times amount (wt ratio) of methanol and 0.5 times amount (wt ratio) of acetic acid, were added and stirred at 40° C. for one hour. After the reaction, the solvent was distilled off under a reduced pressure and washed three times with saturated aqueous solution of sodium hydrogencarbonate, and twice with saturated aqueous solution of table salt. By GC measurement of the obtained liquid, it was found that the peak of the compound represented by the general formula (z) and/or (z') disappeared, and the purity was improved from 86.9% to 91.7%, but two peaks based on impurities was observed as a result of the GC measurement.

The structure of the impurities on which the peaks based is uncertain, and it is not suitable for a raw material of ophthalmic lenses.

[Table 1]

TABLE 1

| | Amount of water in the reaction system (weight %) | Purity before column purification (areal % by GC) | Content of the compound represented by the formula (y) (areal % by GC) | Content of the compound represented by the formula (z) and (z') (areal % by GC) | Purity after column purification (areal % by GC) |
|---|---|---|---|---|---|
| Example 1 | 1.7 | 89.8 | 1.72 | 1.9 | 91.4 |
| Example 2 | 1.0 | 91.3 | 1.33 | 1.3 | 92.5 |
| Example 3 | 0.8 | 90.5 | 0.98 | 1.5 | 91.2 |
| Example 4 | 0.5 | 89.2 | 0.72 | 2.5 | 89.8 |
| Example 5 | 0.2 | 87.6 | 0.41 | 3.8 | 88.0 |
| Comparative example 1 | 0 | 86.3 | 0.32 | 5.7 | 86.5 |
| Comparative example 2 | 0 | 86.9 | 0.31 | 5.3 | 91.7 |

INDUSTRIAL APPLICABILITY

This invention can be suitably used as a raw material of a polymer used for ophthalmic lenses, such as a contact lens, an intraocular lens and an artificial cornea.

The invention claimed is:

1. A process for producing of a silicone compound represented by the following formulas (a) and/or (a'),

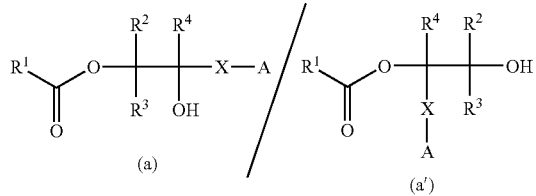

comprising reacting a carboxylic acid represented by the following formula (a2)

to an epoxy silane represented by the following formula (a1)

and
obtaining a metal salt of the carboxylic acid represented by the general formula (a2), wherein the reaction is carried out in presence of 0.8 wt % or more water in said reaction system, wherein A denotes a siloxanyl group, $R^1$ denotes a substituent with 1 to 20 carbons having a polymerizable group, $R^2$ to $R^4$ respectively and independently denote hydrogen, a substituted or unsubstituted substituent with 1 to 20 carbons, or —X-A, and X denotes a substituted or unsubstituted divalent substituent with 1 to 20 carbons.

2. A process for producing of a silicone compound, wherein the silicone compound obtained according to claim 1 is purified by a silica gel column or an alumina column.

3. The process of claim 1, wherein the siloxanyl group A is an atomic group represented by the following formula (b),

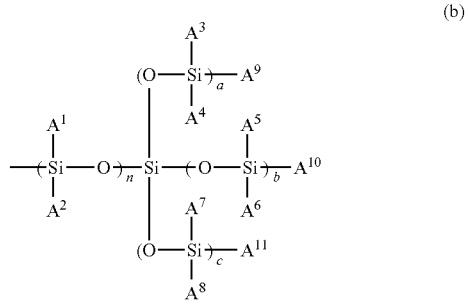

wherein, $A^1$ to $A^{11}$ respectively and independently denote any one of hydrogen, a substituted or unsubstituted alkyl group with 1 to 20 carbon atoms and a substituted or unsubstituted aryl group with 6 to 20 carbons, n denotes an integer of 0 to 200, a, b and c denote respectively and independently an integer of 0 to 20, and n=a=b=c=0 is not included.

4. The process of claim 3, wherein the siloxanyl group A is selected from the group consisting of tris(trimethylsiloxy)silyl group, bis(trimethylsiloxy)methylsilyl group and trimethylsiloxydimethylsilyl group.

5. The process of claim 1, wherein the silicone compound comprises a content of a compound represented by the following general formula (y) in the amount of 0.4% or more and 3% or less,

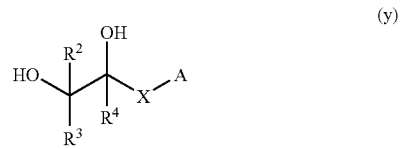

and a purity of the silicone compound is 87% or more.

6. The process of claim 2, wherein the siloxanyl group A is an atomic group represented by the following formula (b), (b) 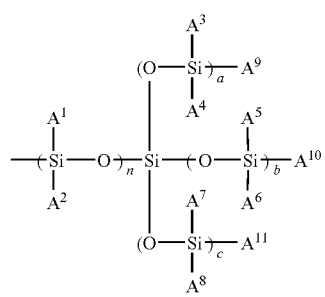
wherein, $A^1$ to $A^{11}$ respectively and independently denote any one of hydrogen, a substituted or unsubstituted alkyl group with 1 to 20 carbon atoms and a substituted or unsubstituted aryl group with 6 to 20 carbons, n denotes an integer of 0 to 200, a, b and c denote respectively and independently an integer of 0 to 20, and n=a=b=c=0 is not included.
* * * * *